(12) United States Patent
Yamaguchi

(10) Patent No.: US 10,020,173 B2
(45) Date of Patent: Jul. 10, 2018

(54) CHROMATOGRAPH MASS ANALYSIS DATA PROCESSING APPARATUS

(75) Inventor: Shinichi Yamaguchi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 13/309,187

(22) Filed: Dec. 1, 2011

(65) Prior Publication Data

US 2012/0075308 A1 Mar. 29, 2012

Related U.S. Application Data

(62) Division of application No. 12/136,381, filed on Jun. 10, 2008.

(30) Foreign Application Priority Data

Jun. 29, 2007 (JP) ................................. 2007-171321

(51) Int. Cl.
*H01J 49/00* (2006.01)
*G01N 30/86* (2006.01)
(Continued)

(52) U.S. Cl.
CPC ...... *H01J 49/0036* (2013.01); *G01N 30/8675* (2013.01); *G06F 19/703* (2013.01);
(Continued)

(58) Field of Classification Search
USPC ........................................... 250/281; 422/70
See application file for complete search history.

(56) References Cited

U.S. PATENT DOCUMENTS

| 4,353,242 A | 10/1982 | Harris et al. |
| 2004/0195500 A1* | 10/2004 | Sachs et al. ................... 250/282 |
| 2009/0020693 A1 | 1/2009 | Yamaguchi |

FOREIGN PATENT DOCUMENTS

| JP | 08-334493 A | 12/1996 |
| JP | 2001-165922 A | 6/2001 |

(Continued)

OTHER PUBLICATIONS

Hopfgartner, Gerard et al. "Triple quadrupole linear ion trap mass spectrometer for the analysis of small molecules and macromolecules," Journal of Mass Spectrometry, 2004, 39, p. 845-855.*

(Continued)

*Primary Examiner* — Lyle Alexander
*Assistant Examiner* — Bryan Kilpatrick
(74) *Attorney, Agent, or Firm* — Sughrue Mion, PLLC

(57) ABSTRACT

A chromatograph mass analysis data processing method for obtaining pertinent information on a compound series including a plurality of compounds whose structures and characters are similar. Based on the data obtained by a chromatograph mass analysis, a two-dimensional isointensity line graph is created and displayed with a retention time and a mass-to-charge ratio on the two axes and with a signal intensity represented with a contour. When the operator specifies a desired range, the data contained in the range specified are collected, the signal intensities along the mass-to-charge ratio axis direction are summed up for every retention time to create a summed mass chromatogram based on the summed value. Simultaneously, the signal intensities along the retention time axis direction are summed up for every mass-to-charge ratio to create a summed mass spectrum based on the summed value. These are then displayed on the same screen of the isointensity line graph.

8 Claims, 4 Drawing Sheets

(51) Int. Cl.
*G01N 30/72* (2006.01)
*G06F 19/00* (2018.01)
*G01D 7/02* (2006.01)

(52) U.S. Cl.
CPC .............. *G01D 7/02* (2013.01); *G01N 30/72* (2013.01); *G01N 30/86* (2013.01); *G01N 30/8679* (2013.01); *G06F 19/708* (2013.01)

(56) References Cited

FOREIGN PATENT DOCUMENTS

| JP | 2007-147464 A | 6/2007 |
| WO | WO 2006/121878 A2 | 11/2006 |

OTHER PUBLICATIONS

"Gas Chromatography—Mass Spectroscopy Background"—"Computerized Instrumentation" section, <http://www.gmu.edu/depts/SRIF/tutorial/gcd/pc.htm>, May 8, 1998.*

Federal Register/ vol. 79, No. 241/ Dec. 16, 2014.*

"Gas Chromatography—Mass Spectroscopy Background," <http://www.gmu.edu/departments/SRIF/tutorial/gcd/gc-ms2.htm>, Jan. 20, 1998.

Staack, Ronald F. et al. "The combination of liquid chromatography/tandem mass spectrometry and chip-based infusion for improved screening and characterization of drup metabolites," Rapid Commun. Mass Spectrom, 2005, 19, p. 618-626.

Japanese Office Action dated Dec. 6, 2011, issued in corresponding Japanese Patent Application No. 2007-171321.

* cited by examiner

CHROMATOGRAPH MASS ANALYSIS DATA
PROCESSING APPARATUS

INCORPORATION BY REFERENCE

This is a divisional Application of U.S. Ser. No. 12/136,381 filed Jun. 10, 2008, which claims priority from Japanese Patent Application No. 2007-171321 filed Jun. 29, 2007, the disclosures of which are incorporated by reference in their entirety.

BACKGROUND OF THE INVENTION

The present invention relates to a chromatograph mass analysis data processing apparatus for processing data collected by a chromatograph mass spectrometer such as a gas chromatograph mass spectrometer (GC/MS) and a liquid chromatograph mass spectrometer (LC/MS).

In chromatograph mass spectrometers such as a GC/MS and LC/MS, data having three dimensions, i.e. a retention time, mass-to-charge ratio, and signal intensity, is collected. The data collected is processed to create a mass chromatogram, mass spectrum, and total ion chromatogram. The mass chromatogram shows the relationship between the retention time and the signal intensity for a specified mass-to-charge ratio, the mass spectrum shows the relationship between the mass-to-charge ratio and the signal intensity for a specified retention time, and the total ion chromatogram shows the relationship between the retention time and the signal intensity without the limitation of mass-to-charge ratio.

Conventional apparatuses of this kind are generally capable of displaying the aforementioned graphs in various forms in order to analyze the result collected as previously described. The apparatus disclosed in Patent Document 1, for example, is capable of displaying a graph in which many lines of chromatograms in different colors are overlapped, or displaying a graph in which many mass chromatograms with base lines slightly shifted along the direction of the longitudinal axis (axis of signal intensity) are overlapped. With this apparatus, it is possible to compare the shapes of plural mass chromatograms with respect to various mass-to-charge ratios and to perform a waveform processing.

One known displaying method for grasping the whole data having the aforementioned three dimensions is creating a graph, as described in Patent Document 2, with a retention time and a mass-to-charge ratio on the mutually orthogonal two axes and with a signal intensity represented with a contour or contours. This graph is hereinafter called "an isointensity line graph." In Patent Document 2, if any retention time is specified by a cursor displayed on the isointensity line graph, a mass spectrum for the retention time is displayed, and if any mass-to-charge ratio is specified by the cursor, a mass chromatogram for the mass-to-charge ratio is displayed.

Patent Document 1: Japanese Unexamined Patent Application Publication No. 2007-147464
Patent Document 2: Japanese Unexamined Patent Application Publication No. 2001-165922

SUMMARY OF THE INVENTION

In the field of development/research of medical supplies and agrichemicals for example, it is often required to examine the series of compounds having similar structures or characters. Although a retention time and a mass-to-charge ratio often have a specific relationship in such compound series, conventional apparatus are not intended for selecting plural components included in a compound series, obtaining its information, and performing the data analysis. Performing this analysis requires complicated operations; hence, obtaining improvement of the working efficiency is difficult.

The present invention is accomplished in view of such problems, and the objective thereof is to provide a chromatograph mass analysis data processing apparatus capable of easily obtaining information on a specified compound series or the like and capable of efficiently analyzing such compound series.

Therefore, the present invention developed to solve the aforementioned problem provides a chromatograph mass analysis data processing apparatus for processing data collected by a chromatograph mass spectrometer in which a chromatograph for separating a sample into components and a mass spectrometer for mass-analyzing the sample components separated by the chromatograph are combined, including:

a) a graph displayer for creating a graph with a retention time and a mass-to-charge ratio on two axes on a plane, and with a signal intensity represented with a contour or contours, or represented by an intensity-discriminable expression equivalent to the contour(s), and for displaying the graph on a display screen;

b) a specifier for allowing a user to specify an intended range on the graph displayed by the graph displayer; and c) a processor for summing up the signal intensities for data included in the range specified by the specifier or for remaining data in which the data included in the range is eliminated, along a direction of a retention time axis and/or a mass-to-charge ratio axis, and for displaying a result.

The chromatograph mass spectrometer used in the present invention is, typically, a liquid chromatograph mass spectrometer or a gas chromatograph mass spectrometer. The mass spectrometer may be any type as long as it is capable of separating and detecting ions according to the mass-to-charge ratio. The means for the mass separation may be, but not specifically limited to, a quadrupole mass filter or a time-of-flight mass analyzer.

The aforementioned graph "with a retention time and a mass-to-charge ratio on two axes on a plane" may be of any form as long as it can express three dimensions: retention time, mass-to-charge ratio and signal intensity. An example of such graphs is a "two-dimensional contour graph" drawn on a plane with a contour line or lines representing the signal intensity on the aforementioned two axes intersecting vertically; another example is a "three-dimensional contour graph" in which the altitude of a signal intensity is represented by a perspective view from a diagonal direction.

In the chromatograph mass analysis data processing apparatus according to the present invention, the specifier may allow the user to set a frame having a certain form and size on a displayed graph through a drag or similar operation using a pointing device (such as a mouse), so that the range surrounded by the frame is specified as the aforementioned range. In the case where it is known in advance that the range to be seen on the graph can be approximately represented by an expression such as a primary expression, it is possible to allow the user to enter that expression and a margin value (this may be a default value) expressing the deviation from the expression, to set the aforementioned range based on it.

In the case where a certain range is specified by the specifier and the data included in the range serves as a target to be analyzed, the processor sums up the signal intensity values which are expressed by each data along the direction of the mass-to-charge ratio axis with respect to each retention time to obtain the summed values for every retention time. Then a mass chromatogram is created by assigning a retention time to one axis and assigning the summed value to the other axis. In general, a mass chromatogram shows the relationship between the retention time and signal intensity of a certain specified mass-to-charge ratio. However, the mass chromatogram obtained in this case almost always shows the relationship between the summed value of the signal intensity in plural mass-to-charge ratios and the retention time, and furthermore, the plural mass-to-charge ratios differ by every retention time (in some cases they may be the same according to the range selected).

In this respect, the mass spectrum created in this invention is different from conventional ones. Therefore, in the following explanations, the mass chromatogram created as previously stated will be called "a summed mass chromatogram" in order to distinguish it from conventional mass chromatograms.

The processor also sums up the signal intensity values which are expressed by each piece of data in the direction of the retention time axis with respect to each mass-to-charge ratio to obtain the summed values for every mass-to-charge ratio. Then a mass spectrum is created by assigning a mass-to-charge ratio to one axis and assigning the summed value to the other axis. However, this mass spectrum is also different from conventional ones as in the case of the aforementioned summed mass chromatogram. In most cases, the mass spectrum shows the relationship between the summed value of a signal intensity in plural retention times, i.e. in the retention time having a certain time range, and the mass-to-charge ratio. Furthermore, the plural retention times are different for every mass-to-charge ratio (in some cases they may be the same according to the range selected) in the mass spectrum.

In this respect, the mass spectrum created as previously described in this invention is different from conventional ones. Therefore, in the following explanations, the mass spectrum created as previously stated will be called "a summed mass spectrum" in order to distinguish it from conventional mass spectrums.

With the chromatograph mass analysis data processing apparatus according to the present invention, if the user specifies an appropriate range in a graph to select one compound series in which a mass-to-charge ratio and a retention time show a specified relationship, a summed mass chromatogram and summed mass spectrum in which a plurality of compounds included in this compound series appear are displayed on the display screen. Therefore, it is possible to obtain the pertinent information on a compound series with a very simple operation and manipulation. By using this, a qualitative analysis and a quantitative analysis can be effectively performed as well.

In the case where a compound included in a specified compound series interferes or hinders the analysis, the summed mass chromatogram or the summed mass spectrum may be created on the remaining data after the data included in the specified range is eliminated. For this purpose, in particular, it is preferable that a plurality of ranges may be simultaneously specified on a graph.

EXPLANATION OF THE NUMERALS

1 . . . Liquid Chromatograph
2 . . . Mobile Phase Container
3 . . . Liquid Sending Pump
4 . . . Injector
5 . . . Column
10 . . . Mass Spectrometer
11 . . . Ionization Chamber
12 . . . Electrospray Nozzle
13 . . . Heating Pipe
14 . . . First Intermediate Vacuum Chamber
15 . . . First Ion Lens
16 . . . Skimmer
17 . . . Second Intermediate Vacuum Chamber
18 . . . Second Ion Lens
19 . . . Analysis Chamber
20 . . . Quadrupole Mass Filter
21 . . . Ion Detector
22 . . . A/D Converter
23 . . . Data Processor
24 . . . Data Memory
25 . . . Controller
26 . . . Input Unit
27 . . . Display Unit
41 . . . Isointensity Line Graph
42 . . . Summed Mass Chromatogram
43 . . . Summed Mass Spectrum

DETAILED DESCRIPTION OF A PREFERRED EMBODIMENT

Figure 1:
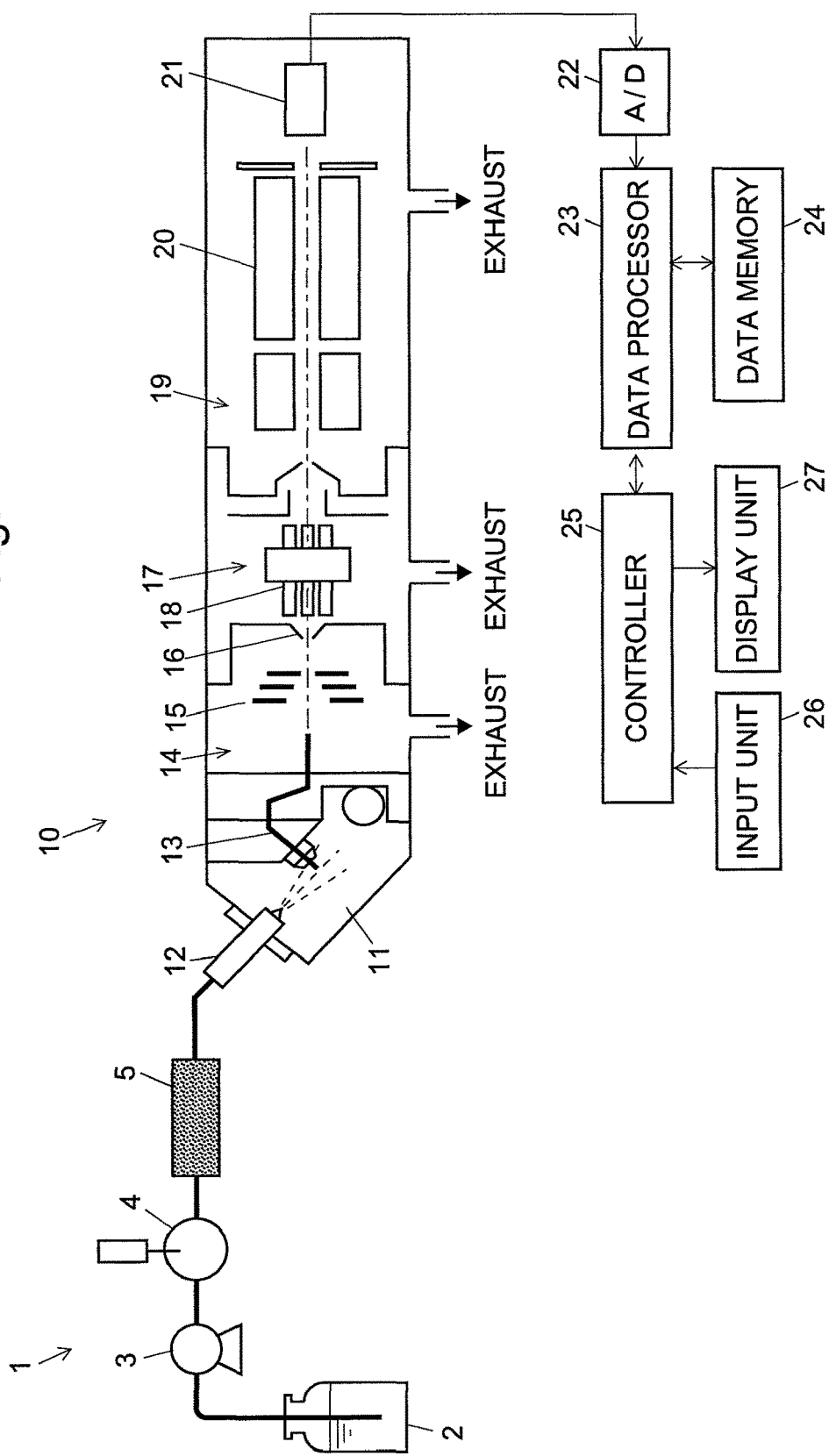
FIG. 1 is a schematic configuration diagram of an LC/MS according to one embodiment of the present invention.

Hereinafter, an embodiment of an LC/MS applying the data processing apparatus according to the present invention will be explained with reference to figures. FIG. 1 is a schematic configuration diagram of an LC/MS according to one embodiment of the present invention.

In the liquid chromatograph 1, a mobile phase held in a mobile phase container 2 is siphoned at an approximately constant flow rate by a liquid sending pump 3 to be provided to a column 5. The sample to be analyzed is introduced to the mobile phase from an injector 4 at a predetermined timing. The sample on the mobile phase is sent into the column 5. While passing through the column 5, various components included in the sample are temporally separated to be eluted from the column 5 in series. The sample liquid including these eluted sample components is introduced to the mass spectrometer 10.

The sample liquid is sprayed into the ionization chamber 11 of an atmosphere of approximate atmospheric pressure from the electrospray nozzle 12, which ionizes the component molecules in the sample liquid. The ions generated are sent into the first intermediate vacuum chamber 14, which is in a low vacuum atmosphere, by way of a heating pipe 13.

In the ionization chamber 11, other atmospheric ionization methods such as an atmospheric chemical ionization can be used other than the electrospray ionization method. Alternatively, such methods may be combined. Whatever the case may be, the ions are sent into the second intermediate vacuum chamber 17, which is in a medium vacuum atmosphere, via a small opening formed on top of a skimmer 16, while being converged by the first ion lens 15 arranged inside the first intermediate vacuum chamber 14. Then the ions are sent into the analysis chamber 19, which is in a high vacuum atmosphere, while being converged by an octapole-type second ion lens 18 arranged inside the second intermediate vacuum chamber 17.

In the analysis chamber 19, only the ions having a specific mass (mass-to-charge ratio m/z to be exact) fly through the longitudinal space of the quadrupole mass filter 20, and ions having other masses are dispersed on the way. The ions that have flown through the quadrupole mass filter 20 reach an ion detector 21, and then the ion detector 21 provides an ion intensity signal corresponding to the ions' amount. This ion intensity signal is converted to a digital value by an A/D converter (analog to digital converter) 22 and then provided to a data processor 23. The data processor 23 creates a mass spectrum, mass chromatogram, total ion chromatogram, etc, and also creates a summed mass chromatogram and summed mass spectrum, which are characteristic of the present embodiment. Based on such results, the data processor 23 performs a qualitative analysis, quantitative analysis, or other analyses. The data processor 23 includes a data memory 24 which stores and saves the data collected by the LC/MS.

To the controller 25 for controlling each unit in order to perform a mass analyzing operation as previously described, an input unit 26, such as a keyboard and mouse, and a display unit 27, such as an LCD (liquid crystal display) are connected. The substance of the data processor 23 and the controller 25 is a personal computer. When the personal computer performs a dedicated control/processing program installed on the personal computer, the functions of the data processor 23 and the controller 25 are realized.

In the LC/MS having the aforementioned configuration, the mass of the ions that are allowed to fly through the quadrupole filter 20 is determined according to the voltage applied to the quadrupole filter 20. Hence, if the voltage applied to the quadrupole filter 20 is repeatedly scanned in a predetermined range from the point in time of the sample's injection (that is, a scan measurement is performed), mass spectrums in a predetermined mass range can be repeatedly obtained as time progresses. Thus the data having three dimensions of a retention time, mass-to-charge ratio, and signal intensity can be collected. The data collected with regard to one sample is stored in the data memory 24 as one file.

Figure 2:
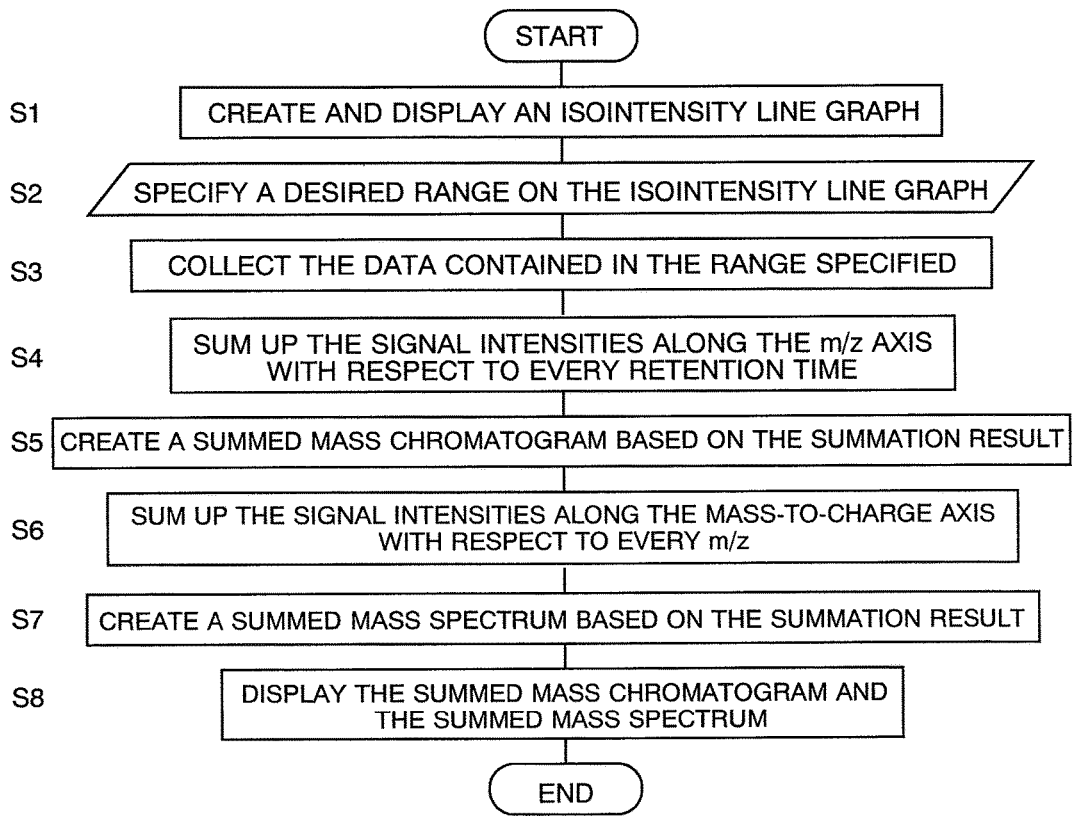
FIG. 2 is a flowchart illustrating the processing procedure of the characteristic data processing in the LC/MS according to the present embodiment.
Figure 3:
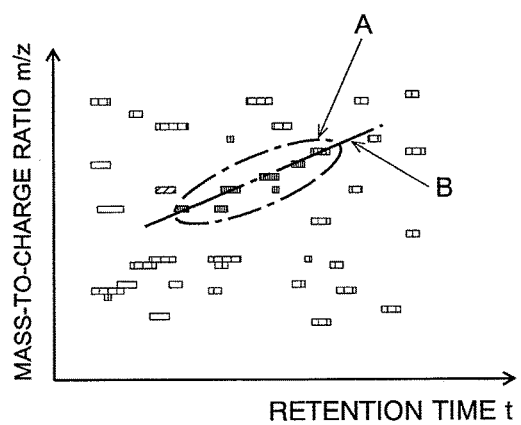
FIG. 3 is a diagram illustrating an example of an isointensity line graph displayed on the screen of the display unit in the LC/MS according to the present embodiment.
Figure 4:
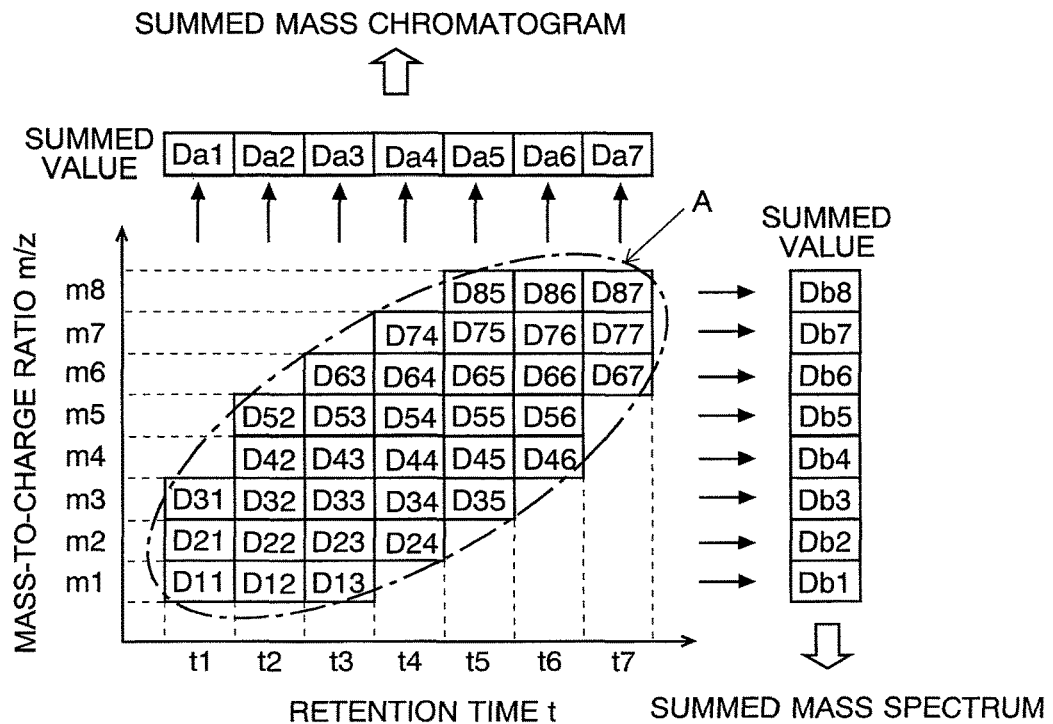
FIG. 4 is a conceptual diagram for explaining the data processing method in the LC/MS according to the present embodiment.

Next, a characteristic data processing in the LC/MS according to the present invention will be explained with reference to FIG. 2 through FIG. 4. FIG. 2 is a flowchart illustrating the processing procedure of this characteristic data processing. FIG. 3 is a diagram illustrating an example of a graph displayed on the screen of the display unit 27. FIG. 4 is a conceptual diagram for explaining the data processing method.

The data processor 23 creates a two-dimensional isointensity line graph based on the data, which is stored in the data memory 24, having three dimensions as previously described. In the isointensity line graph, a retention time is assigned to the horizontal axis, a mass-to-charge ratio is assigned to the longitudinal axis, and a signal intensity is represented with a contour or contours. The data processor 23 displays this graph on the screen of the display unit 27 via the controller 25 (Step S1). FIG. 3 illustrates this isointensity line graph. The operator looks at this isointensity line graph and specifies a range to be analyzed by a drag operation with a mouse (or with another pointing device) of the input unit 26 (Step S2). In FIG. 3, the specified range is shown by a frame A (elliptical shape) of an alternate long and short dash line. The range can be of any form and can be specified at any position. In addition, such a specifying method is not limited to any particular method.

In the isointensity line graph, a series of spots corresponding to a plurality of components having similar structures appears along the positive-slope line B in FIG. 3 for example. Hence, if a compound series including such compounds is required to be selectively analyzed, the frame A can be specified so as to surround the spots along the line B.

If the operator indicates to perform an analysis after specifying a range on the isointensity line graph as just described, the data processor 23 which has received the direction collects the data included in the range specified from the data memory 24 (Step S3). From this point, the explanation will be made using a conceptual diagram illustrated in FIG. 4 in order to simplify the explanation. The specified range extends over the range of t1 through t7 in a retention time and the range of m1 through m8 in a mass-to-charge ratio; a total of 34 pieces of data of D11 through D87 illustrated in FIG. 4 are included in the range. In this figure, a piece of data described as "D11" for example represents a piece of data having the three dimensions of retention time t1, mass-to-charge ratio m1, and signal intensity D11.

After the data included in the range specified as described earlier are collected, the data processor 23 sums up the signal intensities of each retention time along the direction of the mass-to-charge ratio axis, i.e. the longitudinal axis (Step S4). That is, in the retention time t1 for example, since three pieces of data of D11, D21 and D31 exist in the direction of the mass-to-charge ratio axis, the signal intensities of these three pieces of data are summed up to obtain the summed value Da1 with respect to the retention time t1. In the retention time t2 which follows the retention time t1, since five pieces of data of D12, D22, D32, D42 and D52 exist in the direction of the mass-to-charge ratio axis, the signal intensities of these five pieces of data are summed up to obtain the summed value Da2 with respect to the retention time t2. In the same manner, the summed values Da3 through Da1 with respect to the retention times t3 through t7 are sequentially obtained.

For the summed values (summed value of the signal intensities) represented by Da1 through Da7 which were obtained as previously described, a summed mass chromatogram with the retention time as its horizontal axis is created (Step S5). In this summed mass chromatogram, the range of the retention time is limited between t1 through t7. At the same time, the summed mass chromatogram shows a signal intensity not with respect to a certain single mass-to-charge ratio but with respect to a plurality of mass-to-charge ratios and with respect to the different mass-to-charge ratios for each retention time (it could be the same). As described earlier, if the frame A is set so that one certain compound series is specified, the peaks corresponding to the compounds included in the compound series appear in the summed mass chromatogram.

The data processor 23 also sums up the signal intensities along the direction of retention time axis, i.e. along the direction of the horizontal axis (Step S6). That is, since three pieces of data of D11, D12 and D13 exist along the direction of the retention time axis in the mass-to-charge ratio m1, the summed value Db1 in the mass-to-charge ratio m1 is obtained by summing up the intensities of these three pieces of data. Since four pieces of data of D21, D22, D23 and D24 exist along the direction of the retention time axis in the mass-to-charge ratio m2 which is the second smallest value after the mass-to-charge ratio m1, the summed value Db2 with respect to the mass-to-charge ratio m2 is obtained by summing up the intensities of these four pieces of data. In the same manner, the summed values Db3 through Db8 with respect to the mass-to-charge ratios m3 through m8 are sequentially obtained.

Subsequently, for the summed values (summed value of the signal intensities) represented by Db1 through Db8 which were obtained as described earlier, a summed mass spectrum with the mass-to-charge ratio as its horizontal axis is created (Step S7). In this summed mass spectrum, the range of the mass-to-charge ratio is limited between m1 through m8. In addition, the summed mass spectrum shows the signal intensity not with respect to a certain single retention time but with respect to the plural retention times and with respect to the different retention times for each mass-to-charge ratio (it could be the same). As described earlier, if the frame A is set so that one certain compound series is specified, the peaks corresponding to the compounds included in the compound series appear in the summed mass spectrum.

Figure 5:
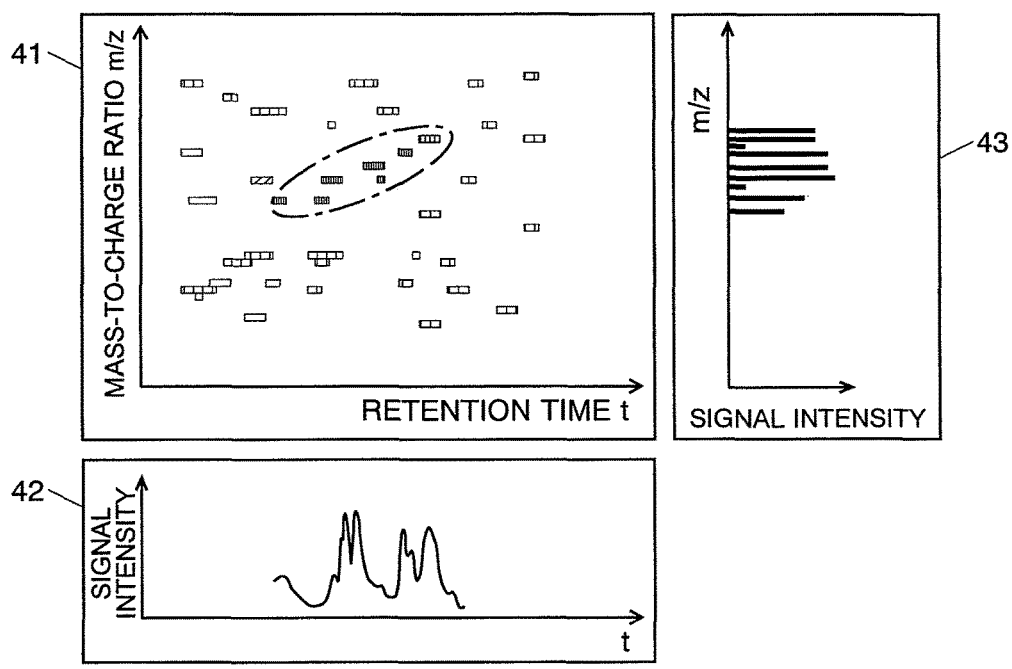
FIG. 5 is a diagram illustrating an example of a display format of an isointensity line graph, summed mass chromatogram, and summed mass spectrum.

The summed mass chromatogram and the summed mass spectrum created in this manner are displayed on the screen of the display unit 27 (Step S8). For example, as illustrated in FIG. 5, an isointensity line graph 41 is placed in a window, a summed mass chromatogram 42 with the same retention time axis' span as that of the isointensity line graph 41 is placed underneath the isointensity line graph 41, and a summed mass spectrum 43 with the same mass-to-charge ratio axis' span as that of the isointensity line graph 41 is placed on the right side of the isointensity line graph 41. With such display, the operator can obtain the pertinent information on each compound included in the compound series to be targeted. In addition, a qualitative analysis and quantitative analysis can be performed using such summed mass chromatogram and summed mass spectrum according to necessity.

The operations of Steps S4 and S5 and the operations of Steps S6 and S7 can be interchanged. If possible, they may be performed in parallel.

Figure 6:
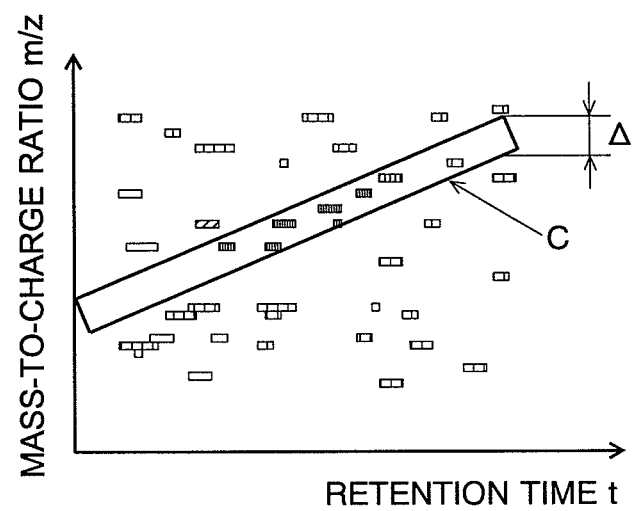
FIG. 6 is a diagram illustrating an example of a range set on an isointensity line graph by another range specification method.

Although in the aforementioned explanation, the range to be analyzed was graphically specified on a two-dimensional isointensity line graph using a pointing device (such as a mouse), the range to be analyzed may be specified by other methods. As an example, a function, e.g. a primary expression, showing the relation between the retention time and the mass-to-charge ratio may be provided through a keyboard serving as the input unit 26. However, a primary expression will be simply a straight line on a graph. Therefore, it is preferable that the thickness of the primary expression, i.e. the straight line, may be set with a margin value or the like. For example, in the case where the relationship between the retention time RT and the mass-to-charge ratio m/z is expressed as:

$$m/z = A \cdot RT + B,$$

the values for A and B can be properly entered and A can be set as the margin value for m/z. With such a setting, a belt-like frame C is set on the isointensity line graph as illustrated in FIG. 6. For the data contained in the range surrounded by this frame C, the process as previously described will be performed to obtain a summed mass chromatogram and a summed mass spectrum.

In the aforementioned embodiment, the summed mass chromatogram and the summed mass spectrum are created using the data contained in a specified range, e.g. ranges surrounded by the frames A or C, on the isointensity line graph. Contrary to this, it is also possible to create a summed mass chromatogram and a summed mass spectrum using the data other than those contained in the range surrounded by the frames A or C. This method is useful in the case, for example, where a plurality of peaks of the compounds having a relatively large signal intensity interfere; such peaks are eliminated so that only a peak or peaks of the compound to be targeted can be studied.

Of course, the method for specifying a range at an intended position and with an intended size on an isointensity line graph is not limited to those described earlier. In addition, the number of ranges to be specified may not be only one but could be any number.

It should be noted that every embodiment described thus far is merely an embodiment of the present invention, and that any modification, adjustment, addition or the like properly made within the spirit of the present invention is also covered within the scope of the present invention. For example, although the present invention was applied to the LC/MS in the aforementioned embodiment, it can be applied to a GC/MS as well. In addition, the mass spectrometer is not limited to the quadrupole type, but could be any type of mass spectrometer such as a time-of-flight type and an ion trap type.

What is claimed is:

1. A method of using a chromatograph mass spectrometer including a chromatograph, a mass spectrometer, a detector, a display screen, and a processor, the processor programmed to create a two-dimensional graph which expresses three dimensions, including retention time, mass-to-charge ratio and intensity of mass spectrum data collected by the chromatograph mass spectrometer, the retention time and the mass-to-charge ratio expressed on two axes on a plane, and the signal intensity represented with a contour or contours, or represented by an intensity-discriminable expression equivalent to the contour(s); the method comprising:

separating a sample into components by a chromatograph of the chromatograph mass spectrometer, mass-analyzing the sample components separated by the chromatograph by a mass spectrometer of the chromatograph mass spectrometer, collecting the retention time and the mass-to-charge ratio of the mass spectrum data of the separated sample components by the detector of the chromatograph mass spectrometer, creating the two-dimensional graph of the mass spectrum data of the separated sample components which expresses three dimensions with the retention time and the mass-to-charge ratio of the mass spectrum data collected by the chromatograph mass spectrometer on the two axes on a plane, and with a signal intensity represented with a contour or contours, or represented by an intensity-discriminable expression equivalent to the contour(s) by the processor;

displaying by the processor the graph which expresses the three dimensions on the display;

allowing a user to graphically specify an area in which a mass-to-charge ratio and a retention time show a specified relationship on the plane with a retention time and a mass-to-charge ratio using a frame on two axes on the graph which expresses three dimensions by the processor;

summing up the signal intensities for data included in the area specified on the retention time and the mass-to-charge ratio or for remaining data in which the data included in the range is eliminated by the processor;

displaying by the processor a two-axes result showing summed intensity values for all mass-to-charge ratios of the data or the remaining data plotted along a retention time axis and/or a two-axes result showing summed intensity values for all retention times of the data or the remaining data plotted along a mass-to-charge ratio axis whereby the user's ability to obtain pertinent information on the sample components is improved; and in the summing up step, the signal intensities of each retention time along a direction of the mass-to-charge ratio axis are summed up to create a summed mass chromatogram where a range of the mass-to-charge ratios whose signal intensities are summed up is different from a retention time to another retention time.

2. The method according to claim 1, wherein the graph is a two-dimensional contour graph drawn on a plane with a contour line or lines representing the signal intensity on the mass-to-charge ratio axis and the retention time axis intersecting vertically.

3. The method according to claim 2, wherein summing up the signal intensities comprises summing up the signal intensities of each retention time along a direction of the mass-to-charge ratio axis to create a summed mass chromatogram, further comprising displaying the summed mass chromatogram with the two-dimensional contour graph.

4. The method according to claim 2, wherein summing up the signal intensities comprises summing up the signal intensities of each mass-to-charge ratio along a direction of the retention time axis to create a summed mass spectrum, further comprising displaying the summed mass spectrum with the two-dimensional contour graph.

5. The method according to claim 1, wherein allowing the user to specify the area comprises allowing the user to set the frame having a predetermined form and size on a displayed graph through a predetermined operation using a pointing device so that a range surrounded by the frame is specified as the aforementioned range.

6. The method according to claim 1, wherein allowing the user to specify the area comprises allowing the user to enter an expression showing a relationship between the retention time and the mass-to-charge ratio.

7. The method according to claim 6, further comprising allowing the user to enter a margin value expressing a deviation from the expression.

8. The method according to claim 6, wherein the expression is a primary expression.

* * * * *